United States Patent
Huang (10) Patent No.: US 10,640,766 B2
(45) Date of Patent: May 5, 2020

(54) BIOSENSORS FOR CHLORIDE IONS

(71) Applicant: Tempo Bioscience, Inc., San Francisco, CA (US)

(72) Inventor: Angela Huang, San Mateo, CA (US)

(73) Assignee: TEMPO BIOSCIENCE, INC., San Francisco, CA (US)

( * ) Notice: Subject to any disclaimer, the term of this patent is extended or adjusted under 35 U.S.C. 154(b) by 232 days.

(21) Appl. No.: 15/949,694

(22) Filed: Apr. 10, 2018

(65) Prior Publication Data

US 2019/0112597 A1 Apr. 18, 2019

Related U.S. Application Data

(60) Provisional application No. 62/484,425, filed on Apr. 12, 2017.

(51) Int. Cl.

| | | |
|---|---|---|
| *C07K 14/705* | (2006.01) | |
| *C12N 15/10* | (2006.01) | |
| *G01N 33/84* | (2006.01) | |
| *G01N 33/68* | (2006.01) | |
| *G01N 33/52* | (2006.01) | |
| *C12N 5/0735* | (2010.01) | |
| *C12N 5/0789* | (2010.01) | |
| *C12N 5/077* | (2010.01) | |
| *C12N 5/074* | (2010.01) | |
| *C12N 15/52* | (2006.01) | |
| *C12N 15/85* | (2006.01) | |

(52) U.S. Cl.
CPC ........ *C12N 15/1086* (2013.01); *C07K 14/705* (2013.01); *C12N 5/0606* (2013.01); *C12N 5/0647* (2013.01); *C12N 5/0656* (2013.01); *C12N 5/0696* (2013.01); *C12N 15/52* (2013.01); *C12N 15/85* (2013.01); *G01N 33/52* (2013.01); *G01N 33/68* (2013.01); *G01N 33/84* (2013.01); *C07K 2319/03* (2013.01); *C07K 2319/033* (2013.01); *C07K 2319/05* (2013.01); *C07K 2319/60* (2013.01); *C12N 2015/859* (2013.01); *G01N 2333/705* (2013.01)

(58) Field of Classification Search
CPC .... C12N 15/1086; C12N 15/52; C12N 15/85; C12N 5/0606; C12N 5/0647; C12N 5/0656; C12N 5/0696; C12N 2015/859; G01N 33/52; G01N 33/68; G01N 33/84; G01N 2333/705; C07K 14/705; C07K 2319/03; C07K 2319/05; C07K 2319/033; C07K 2319/60
See application file for complete search history.

(56) References Cited

U.S. PATENT DOCUMENTS

| | | |
|---|---|---|
| 2014/0010861 A1 | 1/2014 | Bancel et al. |
| 2015/0307888 A1 | 10/2015 | Malphettes |
| 2016/0178635 A1 | 6/2016 | Huang |
| 2017/0205400 A1 * | 7/2017 | Berger .................. C12Q 1/485 |

FOREIGN PATENT DOCUMENTS

| | | |
|---|---|---|
| WO | WO 2013/016418 | 1/2013 |
| WO | WO 2015/193466 | 12/2015 |

OTHER PUBLICATIONS

Kim EB, et al. (Oct 12, 20100) Nature. 479(7372):223-7. (doi: 10.1038/nature10533).*
Arosio D, et al. (2010) Nature Methods. 7:516-518. (doi: 10.1038/nmeth.1471).*
Sato SS, et al. PNAS. E8770-8779. published online Sep. 26, 2017. (www.pnas.org/cgi/doi/10.1073/pnas.1702861114).*
Genebank sequence: NM_001829/NM_001829.3 = *Homo sapiens* chloride voltage-gated channel 3 (CLCN3), transcript variant b, mRNA.
PCT Search Report and Written Opinion.

* cited by examiner

*Primary Examiner* — Robert S Landsman
(74) *Attorney, Agent, or Firm* — Eric P. Mirabel, JD, LLM (57) ABSTRACT

This invention provides biosensors, cell models, and methods of their use for monitoring chloride ion, where the biosensors can include targeting domains, sensing domains and reporting domains. Biosensors can be introduced into cells reprogrammed to represent experimental or pathologic cells of interest, including as detectors of chloride ions, as TempoChloro™ accomplishes.

10 Claims, 3 Drawing Sheets
(3 of 3 Drawing Sheet(s) Filed in Color)
Specification includes a Sequence Listing.

FIG. 1

LEGEND

Black bar: Control Hepes buffer (Far left)
Red bar: 0.1mM NaCl HBSS pH 7.4 (Second from left)
Gray bar: HBSS pH 3.0 (Second from right)
Blue Bar: Picrotoxin 10µM (Right)

FIG. 2

LEGEND
Red Lines: 0.1mM NaCl HBSS pH 7.4 (Uppermost)
Blue Lines: Picrotoxin 10µM (Next uppermost)
Black Lines: HBSS pH 3.0 (Third uppermost)
Gray Lines: Control Hepes buffer (Lowest)

FIG. 3

LEGEND
Black bar: Control Hepes buffer (Left)
Red bar: HBSS pH 3.0 (Middle)
Blue Bar: 0.1mM NaCl HBSS pH 7.4 (Right)

BIOSENSORS FOR CHLORIDE IONS

SEQUENCE LISTING

The instant application contains a Sequence Listing which has been submitted electronically in ASCII format and is hereby incorporated by reference in its entirety. Said ASCII copy, created on Apr. 13, 2018, is named TEMPO-CHLORO_SL.txt and is 15,183 bytes in size.

BACKGROUND

Detection of voltage potentials and changes to the internal ionic environment of cells can be useful in monitoring bioactivities of cells. For example, many cells experience significant changes in internal calcium ion ($Ca^{2+}$) concentration in response to binding of a ligand to a G-protein receptor. In another aspect, certain cells experience large changes in voltage potential across membranes, e.g., in response to contact with neurotransmitters at a synapse. Such cellular changes are responsible for important functions in cells and can be indicative of the health, function, or development processes of the cells.

Chloride is another important ion, particularly for cellular homeostasis. Sodium and potassium ions are moved across cell membranes passively or by an active transport system—the sodium-potassium pump—and chloride ions are actively transported by the chloride ion pump. The chloride ion pump is important for controlling sweat, digestive juices and mucus; and for maintaining cellular homeostasis and blood pH. In cystic fibrosis, a genetic defect results in a misshapen chloride ion pump. Chloride levels within the cells are not controlled properly, and the cells produce thick mucus. Disruption of chloride ions is also implicated in diseases associated with inflammation, and is important for controlling blood pH.

In studying intracellular chloride levels in response to products with treatment potential, signal transduction studies are carried out in cell types that are not representative of the actual cells of interest. For example, researchers may be limited to studying signaling agents and potential therapeutics in rodents or immortal cell lines in vitro, which often provide results not repeated in human cells, or clinical patients. Researchers may create host cells for study by introduction of oncogenes to primary cell lines, e.g., with differentiation to a cell type of choice. However, such host cells or cells generated cannot be relied on to respond normally on contact with bioactive agents.

A need therefor exists for model cell systems representative of cells and tissues existing in live animal systems of interest. It would be desirable to have chloride sensor peptide constructs that can be targeted to specific intracellular locations. Benefits would also be realized if systems were available allowing three dimensional signal detection in mock tissues of representative cells in vitro. These systems would be useful for screening and identifying and confirming efficacy of bioactive agents.

SUMMARY

The biosensors of the invention are capable of detecting changes in chloride ion concentrations. They can be used, e.g., in human iPSCs-derived cell types to image 2D or 3D cellular models of cells expressing certain pathologies. Such models can be useful in screening and evaluation of candidate drug compounds for chemical, biologic, therapeutic, and toxicological effects in humans or in other mammalian species (including companion animals e.g., dogs and cats, and livestock).

The biosensors can have structures targeting cellular compartments, e.g., the nucleus, cytoplasm, plasma, certain membrane surfaces, and/or the like. They can evaluate and report fluctuations in membrane potentials due to differentials or changes in chloride ion concentrations.

The biosensors can be configured or genetically modified to contain promoter sequences specific to certain cell types, e.g., dopaminergic neurons, GABAergic neurons, astrocytes, cardiomyocytes, immortalized human cancer cell lines, HSCs, NPCs, human or mammalian cells in general and/or MSCs.

In one embodiment, the chloride ion biosensor is a peptide construct including a chloride ion sensing domain (which incorporates a transmembrane domain) and a reporter domain. The transmembrane domain is preferably adapted to integrate into a membrane of a human cell. The reporter domain is preferably a fluorescent reporter domain. The fluorescent reporter may fluoresce at wavelengths in the range from 500 nm to 1400 nm, and preferably has a fluorescent emission range of 500 nm-700 nm and a fluorescent excitation range of 400 nm-700 nm. The biosensor may preferably change conformation (e.g., when the chloride ion sensing domain is activated), resulting in the fluorescent reporter domain changing its fluorescent emission characteristics.

In certain embodiments of the chloride ion sensing domain is a sensor peptide at least 70%, 80%, 90%, 95%, 98%, or 99% identical to:

(SEQ ID NO: 1)
MAGCRGSLCCCCRWCCCCGERETRTPEELTILGETQEEEDEILPRKDYES

LDYDRCINDPYLEVLETMDNKKGRRYEAVKWMVVFAIGVCTGLPVAAGSG

IPEIKCYLNGVKVPGIVRLRTLLCKVFGVLFGVAGGLFVGKEGPMIHSGA

VVGAGLPQFQSISLRKIQFNFPYFRSDRDKRDFVSAGAAAGVAAAFGAPI

GGTLFSLEEGSSFWNQGLTVVKVLFCSMSATFTLNFFRSGIQFGSWGSFQ

LPGLLNFGEFKCSDSDKKCHLWTAMDLGFFVMMGVIGGLLGATFNCLNKR

LAKYRMRNVHPKPKLVRVLESLLVSLVTTVVVFVASMVLGECRQMSSSSQ

ISNGSFQLQVTSEDVNSSIKTFFCPNDTYNDMATLFFNSQESAILQLFHQ

DATFLVCSFTSYIGLGHIYSGTFALIGAAAFLGGVVRMTISLTIILIEST

NEITYGLPIMVTLMVAKWTGDFFNKGIYDIHVGL.

SEQ ID NO:1 is encoded by the following g DNA sequence:

(SEQ ID NO: 2)
atggcgggctgccgcggcagcctgtgctgctgctgccgctggtgctgctg ctgcggcgaacgcgaaacccgcacccggaagaactgaccattctgggcg aaacccaggaagaagaagatgaaattctgccgcgcaaagattatgaaagc ctggattatgatcgctgcattaacgatccgtatctggaagtgctggaaac catggataacaaaaaaggccgccgctatgaagcggtgaaatggatggtgg tgtttgcgattggcgtgtgcaccggcctgccggtggcggcgggcagcggc attccggaaattaaatgctatctgaacggcgtgaaagtgccgggcattgt -continued
gcgcctgcgcaccctgctgtgcaaagtgtttggcgtgctgtttggcgtgg cgggcggcctgtttgtgggcaaagaaggcccgatgattcatagcggcgcg gtggtgggcgcgggcctgccgcagtttcagagcattagcctgcgcaaaat tcagtttaactttccgtattttcgcagcgatcgcgataaacgcgattttg tgagcgcgggcgcggcggcgggcgtggcggcggcgtttggcgcgccgatt ggcggcaccctgtttagcctggaagaaggcagcagcttttggaaccaggg cctgacctggaaagtgctgattgcagcatgagcgcgaccatacccctgaac ttattcgcagcggcattcagtaggcagctggggcagcatcagctgccggg cctgctgaactaggcgaatttaaatgcagcgatagcgataaaaaatgcca tctgtggaccgcgatggatctgggcattagtgatgatgggcgtgattggc ggcctgctgggcgcgaccataactgcctgaacaaacgcctggcgaaatat cgcatgcgcaacgtgcatccgaaaccgaaactggtgcgcgtgctggaaag cctgctggtgagcctggtgaccaccgtggtggtgtttgtggcgagcatgg tgctgggcgaatgccgccagatgagcagcagcagccagattagcaacggc agattcagctgcaggtgaccagcgaagatgtgaacagcagcattaaaacc tttttttgcccgaacgatacctataacgatatggcgaccctgttttttaa cagccaggaaagcgcgattctgcagctgtttcatcaggatgcgacctact ggtgtgcagattaccagctatattggcctgggccatatttatagcggcac ctttgcgctgattggcgcggcggcgtttctgggcggcgtggtgcgcatga ccattagcctgaccattattctgattgaaagcaccaacgaaattacctat ggcctgccgattatggtgaccctgatggtggcgaaatggaccggcgattt ttttaacaaaggcatttatgatattcatgtgggcctg.

Variants of SEQ ID NO: 1 are encoded by variants of SEQ ID NO: 2 (where such variants include all degenerate DNA sequences which encode specific variants of SEQ ID NO: 1).

The fluorescent reporter domain peptide includes a fluorescent domain comprising a sequence at least 70%, 80%, 90%, 95%, 98%, or 99% identical to:

(SEQ ID NO: 3)
MYTDCKEFSNTYHNLGRLPDEDRHWSASCHHHHHHMGMSGSSMSV

IKSHNVMVSKGEELFTGVVPILVELDGDVNGHKFSVRGEGEGDATNGKLT

LKFICTTGKLPVPWPTLVTTFGYGVACFSRYPDHMKQHDFFKSAMPEGYV

QERTISFKDDGTYKTRAEVKFEGDTLVNRIELKGIDFKEDGNILGHKLEY

NFNSHYVYITADKQKNSIKANFKIRHNVEDGSVQLADHYQQNTPIGDGPV

LLPDNHYLSHQSKLSKDPNEKRDHMVLLEFVTAAGITLGMDELYKSGLRS

RAQASNSAVDGTAGPGSTGSR.

SEQ ID NO: 3 is encoded by the following DNA sequence:

(SEQ ID NO: 4)
ATG TAT ACA GAC TGT AAG GAA TTC TCT AAT ACA TAT

CACAAT CTG GGG AGA CTT CCT GAT GAG GAC AGG CAC TGG

AGC GCC TCC TGC CAT CAT CAT CAT CAC CAT ATG GGG

ATG TCT GGCTCA TCT ATG AGC GTA ATC AAG TCC CAC AAT

GTC ATG GTG TCA AAA GGG GAA GAG TTG TTT ACC GGG

GTT GTT CCT ATT CTCGTA GAG TTG GAC GGT GAC GTG AAT

GGT CAC AAG TTC TCC GTT CGC GGC GAA GGA GAG GGT

GAT GCA ACC AAT GGG AAA CTGACC CTG AAA TTC ATA TGC

ACG ACT GGT AAA CTT CCT GTA CCG TGG CCG ACA CTC

GTT ACC ACG TTC GGG TAC GGA GTG GCTTGC TTC TCC AGA

TAC CCC GAC CAC ATG AAA CAA CAC GAC TTT TTC AAA

TCT GCA ATG CCC GAG GGC TAT GTT CAG GAA CGGACC ATA

TCT TTT AAG GAT GAT GGA ACA TAT AAA ACA AGG GCA

GAA GTA AAA TTT GAA GGG GAT ACT TTG GTG AAC AGG

ATAGAG CTC AAA GGG ATA GAT TTT AAG GAG GAC GGA AAT

ATA CTG GGC CAT AAG CTT GAG TAT AAT TTC AAC TCA

CAC TAC GTCTAT ATT ACA GCT GAC AAA CAA AAG AAC AGT

ATC AAA GCG AAC TTC AAG ATT CGC CAT AAT GTC GAA

GAT GGA AGC GTG CAACTC GCC GAC CAT TAT CAG CAG AAC

ACT CCG ATA GGC GAT GGA CCA GTA CTT CTG CCC GAC

AAC CAC TAT TTG AGT CAC CAGAGT AAG TTG AGT AAG GAC

CCT AAC GAG AAG AGA GAT CAC ATG GTC TTG CTC GAA

TTT GTG ACT GCA GCG GGT ATT ACC TTGGGA ATG GAC GAG

CTT TAC AAG TCT GGT CTT AGA TCA CGA GCA CAG GCT

TCA AAT TCT GCA GTA GAT GGT ACA GCC GGA CCCGGG AGC

ACA GGT TCT AGG TAA.

Variants of SEQ ID NO: 3 are encoded by variants of SEQ ID NO: 4 (where such variants include all degenerate DNA sequences which encode specific variants of SEQ ID NO: 3).

The invention also includes a nucleic acid construct encoding any of the chloride ion sensors described herein, and can include a tag sequence including: a nucleus localization signal (NLS) tag, a mitochondrial localization tag, and a ciliary tag. Further, the nucleic acid construct can include a sequence encoding the NLS tag or a sequence with at least 80% identity to the NLS tag peptide sequence: DPKKKRKV (SEQ ID NO: 5).

The invention also includes a human cell expressing the chloride ion sensor described herein. In preferred embodiments, the human cell is an iPSC derived cell. For example, the cell can be derived from induction of a fibroblast or a blood cell to a pluripotent or immortal status. The cell is preferably derived from a human patient derived cell type.

The invention also includes methods of reprogramming and monitoring cells. For example, in a method of reprogramming fibroblasts can include transforming the fibroblasts with one or more constructs comprising a human clock gene and human Bmal1/2/3/4 genes having E-box promoters, synchronizing the circadian rhythm of the fibroblasts, modifying transcriptional regulatory control of the fibroblasts (thereby converting them into inducible pluripotent stem cells), and reprogramming the stem cells into inducible neurons (iN), glial cells, including astrocytes (iG), inducible pluripotent stem cells (iPSCs), or inducible neural progenitor cells (iNPCs). In many of the methods for reprogramming using circadian rhythms of human cell types, the transforming construct comprises a nucleic acid encoding a chloride ion sensor described herein.

The methods can include, e.g., modifying transcriptional control by providing specific transcription factors suitable for a lineage of the fibroblasts. The transcription factors can include the factors specific for a cellular lineage of the fibroblasts modified to include a circadian regulatory element (E-box promoters, an artificial E-box-like promoter sequence tag, a chemical agent that alters or synchronizes circadian rhythms cycles, or a synthetic transcriptional enhancer element) for reprogramming using circadian rhythms of human cell types.

The cellular composition can further include the co-culturing iN cells and iG cells to create a 2D monolayer or a 3D spheroid or organoid model, including on a scaffold in vitro. Cancer cell lines and cancer stem cells can be cultured in such 2D or 3D models using standard culturing hardware and conditions. Biosensor constructs of the invention can be used to image the resultant tissues and monitor changes in chloride ion levels in real time.

The present inventive methods include compositions and techniques for identifying, confirming or screening agents that influence chloride ion levels of cells. For example, methods for screening active agents can include transforming one or more cells with a nucleic acid encoding a chloride ion sensor, expressing the chloride ion sensor in the cells, contacting the cells with candidate active agents, and detecting a change in florescence of the sensor in response to the agent. Typical agents can include, e.g., members of a small molecule chemical library. For example, the agents can be reviewed for an activity resulting from interactions with a chloride ion channel, a receptor, and/or associated signaling pathways.

The methods herein are also useful in imaging live cells in low, medium, and/or high throughput assay formats. For example, cells in 3D arrays, transformed and expressing biosensor constructs of the invention can be viewed in real time, e.g., using microscopic imaging systems. Optionally, biosensor cells in surface or suspension culture can be monitored by detecting fluorescence changes (using monitors made by Molecular Devices, BioTek, or Tecan), confocal imaging or microscopes (including those made by Zeiss, Leica, Nikon, and Olympus), FACS sorters, CCD video imaging, and/or high content imagers (including: GE InCell 2000/6000, PerkinElmer Operetta, and EssenBioscience IncuCyte).

3D cancer cell models have been used as an improved predictor of tumor responses to drug candidates using library screening high throughput screening (HTS) methods. Cells used for such studies aren't limited to immortalized cancer cell lines. Cancer stem cells, primary tissue cells, and 3D printed tissue types can be used for screening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

As used in this specification and the appended claims, the singular forms "a", "an" and "the" include plural referents unless the content clearly dictates otherwise. Thus, for example, reference to "a surface" includes a combination of two or more surfaces; reference to "DNA" "peptide" "protein" "compound" includes, respectively, multiple individual molecules, and the like.

iPSC refers to inducible pluripotent stem cells; iN refers to inducible neurons; iG refers to inducible glial cells (including astrocytes); and iNPCs inducible neural progenitor cells.

Near-Infrared refers to light wavelengths ranging from about 600 nm to about 1400 nm.

The term "conservative variant" includes modifications of given sequences that result in conserved function. For example, in the context of nucleic acids, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

Similarly, conservative variants in the context of peptide sequences can be expected to retain function. For example, Guo, "Protein Tolerance to Random Amino Acid Change", (PNAS 101:9205-10; 2004), demonstrates that one of skill can modify peptides successfully even "without detailed knowledge of the ways in which a protein's structure relates to its functional usefulness . . . " Guo finds only 25% of random mutations lead to substantial loss of activity. Guo extensively discusses how one of skill can take into consideration active site location, alpha helices, beta sheets, hydrophobic interactions, turns and loops, conserved sites and the like to intelligently avoid loss of activity, e.g., by substitution avoidance at key positions or with conservative amino acid substitutions. Further, Guo states that his "database can be a valuable resource for predicting the effects of mutations on protein function . . . " Substitutions to known structures are predictable and in possession the of those having the structural information. Therefore, conservative amino acid substitutions, in which one or a few amino acids in an amino acid sequence are substituted with different amino acids with highly similar properties, are also readily identified as being highly similar to a disclosed constructs, and expected to retain function. One of skill will recognize that individual substitutions, deletions, or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

TABLE 1

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Trytophan (W) | |

The present invention includes biosensor constructs, preparing cells useful in receiving the constructs, cells transformed with the constructs, and assay methods employing the biosensors, e.g., to detect the presence of active agents or signals in living cells.

The biosensors generally include various complementary domain structures working together to sense a voltage or ion at a particular intracellular location, and to provide a distinct signal correlated to changes in the parameter. In a particularly useful embodiment, the biosensors are expressed in cells representative of a particular species (e.g., human), cell type of interest, or in a cell expressing a pathology of interest. Cells expressing the biosensors can be exposed to conditions or agents and monitored for signals indicating cell responses.

Biosensors Generally.

Biosensors of the present invention are generally engineered to include components specialized in providing, e.g., location, sensing, and reporting. In expression of a sensor nucleic acid construct, the peptide product can be positioned within the cell, e.g., by chaperone or transit sequences, hydrophobic affinities, or ligand/receptor interactions. The sensing domains typically change conformation in response to a changed intracellular condition or binding of a signal ion or molecule. Reporting domains display a detectable signal in response to conformational changes in the associated sensing domain.

The intracellular location of a biosensor can optionally be controlled by a targeting domain or "tag." In some biosensors, intracellular location is generalized or passively determined. For example, the sensor may be generally dispersed throughout the nucleus and/or cytoplasm. In other cases, the function or specificity of the biosensor signal may depend on localization at a particular intracellular membrane or organelle. Localizing biosensor tags can be done using hydrophobic peptides which interact with membranes, ionic peptides which disperse in cytoplasm, and/or other chaperone sequences directing the biosensor to a particular compartment including ligands directed to receptors. Tags useful in the study of intracellular signaling and in agent screening assays can include, e.g., NLS tags, lipid membrane tag, endoplasmic reticulum (ER) tags, golgi tags, endosome tags, ciliary tags, and others.

Sensing domains in the biosensors change conformation in response to a changed physical condition, binding of a ligand (peptide or nucleic acid), or a change in an ionic environment, caused, e.g., by interaction with a protease, interaction with a phosphatase, changes in pH, changes in ionic strength, or changes in a voltage potential. The conformational changes can, e.g., cause conformational changes in an associated reporter domain, or reposition the reporter domain to enhance or diminish the signal.

Reporter domains of the biosensors can be of any appropriate type known in the art. However, in preferred embodiments, the reporters comprise one or more peptide domains, e.g., so they can be readily employed in in vivo systems. Typically the peptide reporter domain provides a specific fluorescent emission in response to a specific interrogating excitation wavelength of light. In the context of sensor domain conformational changes, FRET strategies can be effective, e.g., wherein the biosensor construct comprises paired donor/acceptor peptide pairs. In certain embodiments, the reporter domain is adapted to provide an emission in the red to near-infrared spectrum, to allow the signal to pass and be detected in three dimensions through cells or tissue layers. For example, relatively penetrating reporter emission signals can range from 500 nm to 1400 nm, 550 nm to 900 nm, 600 nm to 850 nm, or 500 nm to 800 nm. In the 500 nm-800 nm range, the fluorescent properties can be easily changed to a point within that range, e.g. ~625 nm emission.

In an exemplary embodiment, the reporter domain includes fluorescence enhancing amino acids, such as tryptophan, tyrosine, phenylalanine, which contribute to their intrinsic fluorescence of the domain. Optionally, the reporter domain can include regions naturally modified post-translationally to provide the desired long wavelength emissions. For example, a domain that emits in the red regions can be a modified green fluorescent protein where the fluorophore originates from an internal serine-tyrosine-glycine sequence which is modified to a 4-(p-hydroxybenzylidene)-imidazolidin-5-one structure.

Biosensor constructs can include, e.g., two, three, or four of the above described domain types, in any of a variety of functional configurations. For example, a sensor domain and reporter domain in any order can constitute a biosensor. Often, the biosensors of the invention include at least three domains, e.g., a targeting domain, a sensor domain, and a reporting domain. The three domains can be in any order, but typically the targeting domain is on one end of the construct, the sensor in the middle and the reporter on the second end. In certain configurations, the biosensor construct can be in the order (C-terminal/N-terminal or N-terminal/C-terminal) of: sensor/reporter; targeting/sensor/reporter; targeting/reporter/sensor; targeting/reporter1/sensor/reporter2 (e.g., FRET); reporter1/sensor/reporter2; sensor/reporter1/reporter2; and targeting/sensor/reporter1/reporter2.

Typically, the domains are linked together in a commonly translated construct of a single linear peptide. Optionally, the constructs can include one or more domains not in the same peptide chain as another domain. For example, separate domains may be associated in a non-covalent interaction, such as a hydrophobic interaction, a chelation, a ligand/receptor interaction, an antibody/antigen interaction, and/or the like.

In some cases, a single domain may have more than one function. For example, a sensor domain may also have a structure functioning as a targeting domain. In one embodiment, a domain may have a series of transmembrane domains, acting as both as a sensor (e.g., ligand responsive ion channel) and a membrane specific targeting domain. In another aspect, a sensor domain could also include a reporter function, e.g., acting as a donor or quencher member of a FRET pair with a separate reporter domain.

Chloride Ion Sensing Biosensors.

Chloride ion sensor constructs of the invention include many of the aspects described above for biosensors generally, but the sensor domain is responsive to changes in chloride ion levels. For example, the chloride ion sensor will typically bind Cl⁻ with a certain affinity and change conformation to some degree depending on the local Cl⁻ concentration. Cl⁻ can vary dramatically depending on cell type, condition, and the influence of induced signals. In living cells, Cl⁻ levels often vary with intracellular locations. The present chloride ion sensors can include targeting domains directing the sensors to any intracellular compartment of membrane, such as, e.g., a vacuole, the nucleus, cytoplasm, synapse, endoplasmic reticulum, and/or elsewhere.

Chloride ion sensor domains are typically peptides homologous to portions of one or more chloride ion binding proteins. All that is necessary for the sensor role is that the peptide, or peptide fragment, changes conformation with changes in chloride ion concentration. The change in conformation will translocate the reporter group and typically change the emission profile or intensity. Modern protein engineering techniques can be used to engineer enhancements causing the translocation of the reporter to be enhanced or quenched, e.g., by induced contact or induced conformational changes in the reporter itself.

A preferred chloride ion biosensor construct includes a combination of a tandem array of chloride ion binding domains and a fluorescent peptide. In an exemplary embodiment, the chloride ion sensor includes a modified chloride ion binding domain derived from a known chloride ion binding domain, and a fluorescent protein modified to provide red emissions. The domains of the constructs are typically configured from a combination of bioinformatics/database sequences as modified evolutionary mutagenesis.

SEQ ID NO: 1 is a chloride ion sensing domain. Conservative variations of SEQ ID NO: 1 would be expected to retain substantial sensing function. The present chloride ion binding domains include peptides comprising sequences at least 70%, 80%, 85%, 90%, 95%, 98%, or 99% identical to SEQ ID NO: 1. SEQ ID NO: 3 is a particular reporter domain for the chloride ion sensor peptide. Conservative variations of SEQ ID NO: 3 would be expected to retain substantial useful function. The present fluorescent reporter sensor domains include peptides comprising sequences at least 70%, 80%, 85%, 90%, 95%, 98%, or 99% identical to SEQ ID NO: 3.

Biosensor Constructs in Human or Mammalian Cells.

The biosensors described herein can be incorporated into mammalian cells to monitor chloride ion conditions within the cells. For example, nucleic acid constructs encoding the biosensor peptide domains can be transformed or transfected into eukaryotic cells for expression, e.g., using appropriate promoters, as is known in the art. The cells can be mammalian, preferably human, providing the benefit of a reliable host cell model, e.g., for study of human signal transduction and disease states. The mammalian cells can be immortalized, but are preferably stem cells or cells induced to be pluripotent, or cells induced or otherwise differentiated to become a particular cell type of interest.

The nucleic acid construct can encode any biosensor described herein. For example, the construct can encode a combination of a chloride ion sensor domain, a targeting domain, and/or a reporter domain. In one embodiment, the nucleic acid construct includes transient expression vector components directing expression of peptide chains comprising a combination of domains providing a functional biosensor. For example, the nucleic acid can express a single peptide chain comprising a combination of chloride ion binding domain, troponin domain, and reporter domain. In another example, the nucleic acid construct can encode a peptide comprising at least a combination of a transmembrane domain, a chloride ion sensing domain, and reporter domain.

In other embodiments of the nucleic acid expression constructs, an expression vector includes sequences encoding peptides of any of SEQ ID NOs: 1, 3, or 5. In certain embodiments functioning as chloride ion biosensors, the vector can include a combination of nucleic acid sequences encoding the peptides of SEQ ID NOs: 1 and 3, e.g., along with a sequence encoding a transmembrane domain, such as an ion channel domain. Such a construct can encode functional peptide sequences at least 70%, 80%, 85%, 90%, 95%, 98%, or 99% identical to the sequence of SEQ ID No: 1 and/or SEQ ID NO: 3. The cells transformed with TempoChloro™ used in the experiments shown in FIGS. 1 to 3, were transformed with nucleic acid sequences encoding (C to N terminus) the peptides of SEQ ID NO: 1 and SEQ ID NO: 3, i.e., these cells were transformed using vectors including SEQ ID NOs: 2 and 4.

Useful nucleic acid constructs of the above expression vectors can include additional sequences encoding targeting tags, such as, e.g., a NLS tag, a lipid membrane tag, an ER tag, a golgi tag, an endosome tag, a mitochondrial tag, and/or a ciliary tag. For example, the targeting tag can include a sequence at least 70%, 80%, 85%, 90%, 95%, 98%, or 99% identical to a sequence encoding the peptide tag sequence of SEQ ID NO: 5.

The present inventions include cells comprising the biosensors discussed herein. For example, nucleic acid constructs coding the biosensor peptides can be transduced or transfected into eukaryotic cells of choice. In preferred embodiments, the cells originate from a mammal, preferably from a human. In many embodiments, the cell is an immortalized stem cell, or a cell fully or partially differentiated from a stem cell.

In the context of the present biosensors, cells can be initially derived from patient samples. The advantage of such cells is that they can provide very representative responses to active agents and changed conditions for that patient. Thus, such cell models are more likely to provide information on the modes of action or efficacy of a candidate therapeutic for that patient. For example, such cell models can aid in the identification of custom tailored treatment for patients with certain disease states, such as autoimmune diseases, neurological diseases, cancer, diabetes, or pathologies from genetic flaws.

Alternately, the models can employ cells harboring a particular non-endogenous gene of interest, introduced by genetic engineering techniques. For example, the gene of interest can encode a receptor molecule, a G-protein coupled receptor, or an ion channel of interest. Typically, the host cell is a cell most representative of the cell type of interest in the research. Such model cells can be useful in providing more representative results, e.g., in monitoring a signal transduction or in screening prospective agents active in the modulation of the gene of interest.

Cellular models can be derived from inducible cells available from primary culture of cells from living animals. For example, fibroblasts or undifferentiated cells from circulating blood can be induced to provide pluripotent cells. It is notable that epigenetic processes can play a key role in directing the status of a cell to stem cell, progenitor cell, or mature cell. In Lister (Nature 471 (7336): 68-73, 2011), aberrant epigenomic programming was found capable of inducing a variety of different pluripotent stem cells (iPSCs). Female lung fibroblasts, adipose cells, and foreskin fibroblasts were reprogrammed into induced pluripotent state using OCT4, SOX2, KLF4, and MYC genes. The iPSCs were found to be similar to embryonic stem cells in many characteristics, including DNA methylation patterns. Such concepts can be used to reprogram cells, e.g., in combination with further circadian synchronization techniques, described below.

In addition to inducement by action of immortalizing genes, cell signaling was found to influence epigenetic processes governing differentiation. In the research of Baylin (e.g., Nature Biotechnology 28 (10): 1033-8, 2010), several signaling pathways were suggested as important in the induction and maintenance of embryonic stem cells and in their differentiation. For example, signaling pathways of growth factors can play a role in epigenetic regulation of cellular differentiation. These growth factors include, e.g., transforming growth factors (TGFs), fibroblast growth factors (FGFs), and bone morphogenetic proteins. Another important factor in induction and differentiation can be the Wnt signaling pathway.

Circadian rhythm influences on cellular synchronization can be employed in inducement of pluoripotential cells. For example, cells can be reprogrammed into inducible pluripotent stem cells using human clock gene and human Bmal1/2/3/4 genes and their E-box promoters. In one aspect, fibroblast iPSCs can be generated by such reprogramming, and further directed to provide inducible neurons (iN), glial cells, or inducible neural progenitor cells (iNPCs), as desired. The reprogramming factor for each cell type is typically a transcriptional regulator that is specific for the cellular lineage. Each factor can be modified to be controlled by a circadian regulatory element (such as, E-box promoters or an artificial E-box-like promoter sequence tag). Such promoter sequences can be added to each transcriptional regulator, thus forming a novel transcriptional element for control regulated by human Clock and Bmal genes.

To complement the biosensor systems described herein, induced cells can be cultured together in a "tissue" structure, e.g., in three dimensions. In this way, the cell to cell contacts of interest can be studied, e.g., using penetrating imaging available in the form of near infrared reporter signals. For example, co-cultures of iN and iG can be prepared to create a 3D model of a neuronal structure. The structure can be further controlled, e.g., using an appropriately structured scaffold, e.g., using materials not opaque to reporter signals, e.g., for confocal microscopic review.

Screening and Assay Methods Using Biosensors in Model Cells

The biosensor constructs, e.g., engineered into model cells of interest, can more predictably provide assay and screening results relevant to life science research and study of clinical pathologies of interest. That is, the present targeted biosensors in appropriate cell types, differentiated to a particular phenotype, can provide models more likely to anticipate a normal response in the modeled organism than, e.g., old art xenotypic models.

The initial steps in preparing a model system can be to identify the cell type of interest and the signal to be detected. For example, to study certain therapeutic agents, one may choose to target a chloride ion sensor. Typically the biosensor constructs are transiently expressed in the cells using, e.g., a CMV constitutive promoter or a cell-type-specific promoter.

Once the model system is established, the biosensor can be monitored in a single cell, or across an array of cells. For example, a cell can be exposed to a signaling agent to see if the cell type responds to that agent, e.g., a cytokine or candidate small molecule bioactive agent. Optionally, the cell can be co-transfected with a second expression construct of a peptide of interest (e.g., a tumor-associated antigen or oncogene) to monitor any influence of the external gene in a signaling pathway.

In other embodiments, the cells can be segregated into arrays complementary to low, medium, or high throughput assay formats. For example, cells can be dispensed into 96-well plates, onto a micro-well array, or a FACS sorter, for separate exposure to library members of putative candidate agents. Such arrays can be reviewed suing standard fluorescent detection equipment. Optionally, the arrays can be reviewed photographically with digital CCD based cameras. Changes in a signal, e.g., as compared to a positive or negative reference, can be flagged for additional characterization.

Targeting Tags

In many cases, it is advantageous to direct the chloride ion sensor to a particular intracellular membrane or compartment. The biosensors of the invention can include peptide segments adapted to have an affinity for a cellular target.

Exemplary peptide sequences useful in targeting biosensors to a desired intracellular location include, e.g.:

```
NLS tag (protein sequence):
                                         (SEQ ID NO: 5)
DPKKKRKV.

ER tag:
                                         (SEQ ID NO: 6)
KDEL

Endosome tag:
                                         (SEQ ID NO: 7)
NPTY--DXXLL--YXXoo (protein sequence; tandem
motifs; oo = two residues with hydrophobic side
groups;

Ciliary tag:
                                           SEQ ID NO: 8)
VxPx-RVxP-KVHPSST-AxEGG (protein sequence; tandem
motifs- Human endosome sequence tag
                                         (SEQ ID NO: 9)
MTSRKKVLLKVIILGDSGVGKTSLMHRYVND SEQ ID NO: 10 human synapsin tag:
CCTGCAGGGCCCACTAGTATCTGCAGAGGGCCCTGCGTATGAG

TGCAAGTGGGTTTTAGGACCAGGATGAGGCGGGGTGGGGGTGC

CTACCTGACGACCGACCCCGACCCACTGGACAAGCACCCAACC

CCCATTCCCCAAATTGCGCATCCCCTATCAGAGAGGGGGAGGG

GAAACAGGATGCGGCGAGGCGCGTGCGCACTGCCAGCTTCAGC

ACCGCGGACAGTGCCTTCGCCCCCGCCTGGCGGCGCGCGCCAC

CGCCGCCTCAGCACTGAAGGCGCGCTGACGTCACTCGCCGGTC

CCCCGCAAACTCCCCTTCCCGGCCACCTTGGTCGCGTCCGCGCC

GCCGCCGGCCCAGCCGGACCGCACCACGCGAGGCGCGAGATAG

GGGGGCACGGGCGCGACCATCTGCGCTGCGGCGCCGGCGACTC

AGCGCTGCCTCAGTCTGCGGTGGGCAGCGGAGGAGTCGTGTCG

TGCCTGAGAGCGCAGCTGTGCTCCTGGGCACCGCGCAGTCCGC

CCCCGCGGCTCCTGGCCAGACCACCCCTAGGACCCCCTGCCCCA

AGTCGCAGCC

SEQ ID NO: 11 Human synaptic vesicle tag:
MDCLCIVTTK KYRYQDEDTP PLEHSPAHLP NQANSPPVIV

NTDT LEAPGYELQVNGTEGE MEYEEITLER GNSGLGFSIA

GGTDNPHIG D DPSIFITKIIPGGAAAQDGR LRVNDSILFV
```

-continued

NEVDVREVTH SAAV EALKEA GSIVRLYVMRRKPPAEKVME

IKLIKGPKGL GFSIAGGVG N STSLEITASM

EXAMPLES

Figure 1:
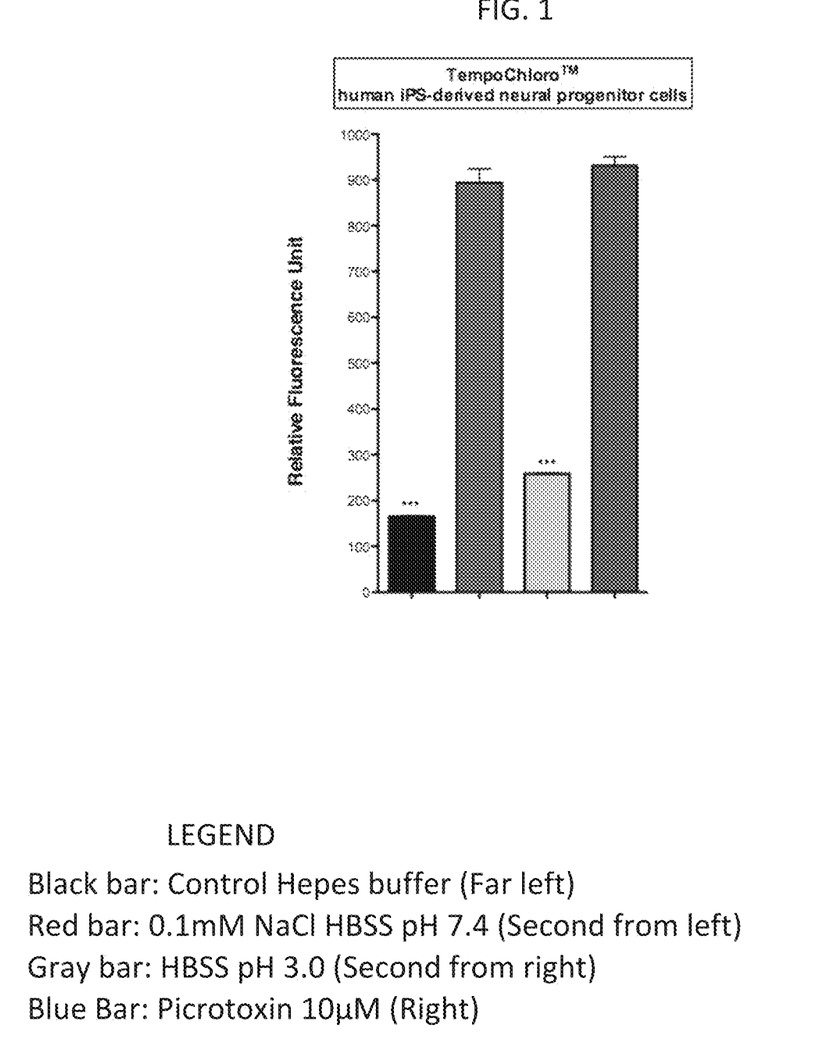
FIG. 1 shows sample identification with the TempoChloro™ biosensor, which is chloride ion sensitive and picrotoxin sensitive, expressed in transformed neural human IPS progenitor cells, where detection is based on relative fluorescence.

FIG. 1 shows the TempoChloro™ biosensor (expressed in transformed neural human IPS progenitor cells) successfully identifying samples with chloride ion or picrotoxin, based on relative fluorescence.

Picrotoxin, also known as cocculin, is a poisonous crystalline plant compound which has been shown to inhibit neurotransmitter GABA-ergic ion channels; acting, in vivo, as a plant-derived stimulant and convulsant. See, Newland, C F; Cull-Candy, S G (February 1992). "On the mechanism of action of picrotoxin on GABA receptor channels in dissociated sympathetic neurones of the rat". The Journal of Physiology. 447: 191-213. doi:10.1113/jphysiol.1992.sp018998. PMC 1176032 Freely accessible. PMID 1317428.

The controls for the assay in FIG. 1 were: HEPES Buffer (pH 7.4 and osmolarity at standard mOsm=300 (+/−15)); 0.1 mM NaCl (1×HBSS buffer pH7.4); and, 10 microMolar Picrotoxin (1×HBSS buffer pH7.4). As a supplemental control against the HBSS buffer in the latter two controls, HBSS buffer pH 3.0 was used. The fluorescence detection parameters were: 517 nm Excitation/535 nm Emission (+/−2).

Figure 2:
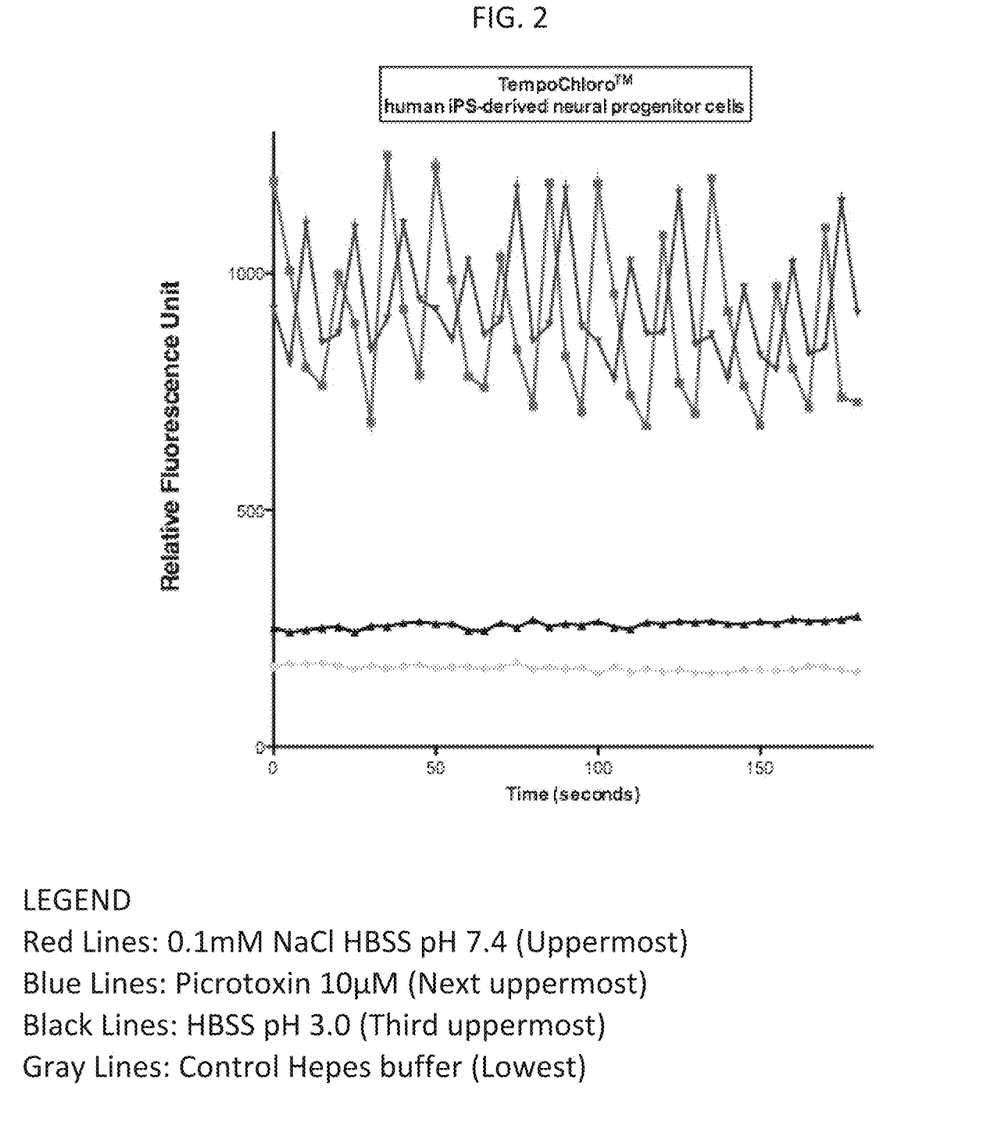
FIG. 2 shows sample identification with the TempoChloro™ biosensor, expressed in transformed neural human IPS progenitor cells, based on relative fluorescence.

FIG. 2 shows the TempoChloro™ biosensor (expressed in transformed neural human IPS progenitor cells) successfully identifying samples with chloride ion or picrotoxin, based on relative fluorescence, as determined by kinetic readouts (X axis shows: seconds per scan). The controls were: HEPES Buffer (pH 7.4 and osmolarity at standard mOsm=300 (+/−15)); 0.1 mM NaCl (1×HBSS buffer pH7.4); and, 10 microMolar Picrotoxin (1×HBSS buffer pH7.4). As a supplemental control against the HBSS buffer in the latter two controls, HBSS buffer pH 3.0 was used. The fluorescence detection parameters were: 517 nm Excitation/535 nm Emission (+/−2).

Figure 3:
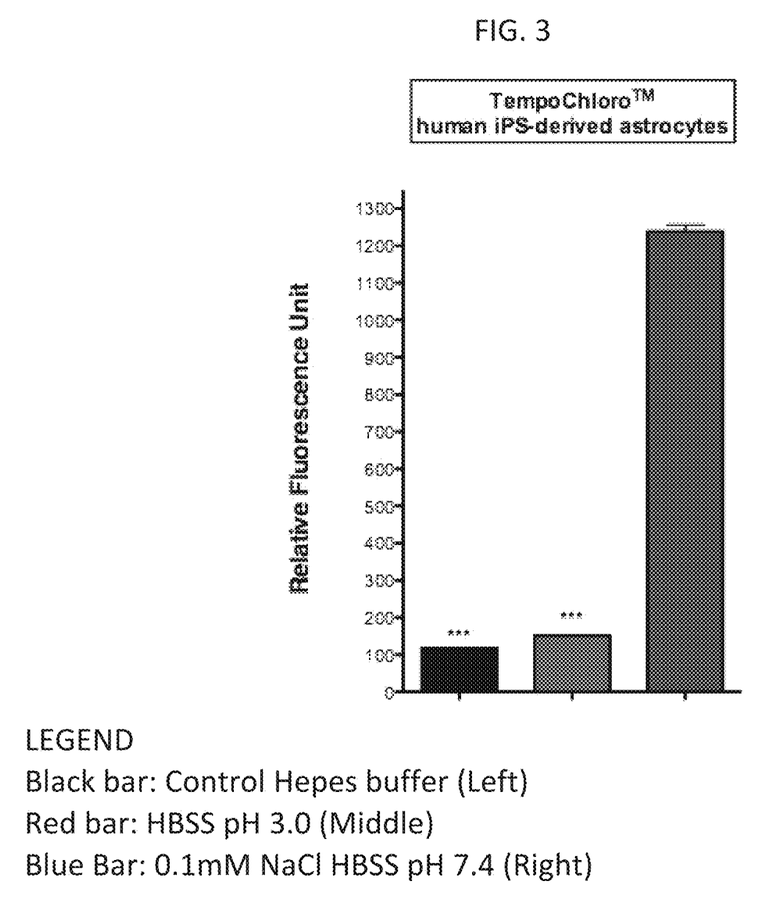
FIG. 3 shows sample identification with the TempoChloro™ biosensor, expressed in human IPS derived astrocytes, based on relative fluorescence.

FIG. 3 shows the TempoChloro™ biosensor (expressed in transformed human iPS-derived astrocytes, which are glial cells) successfully identifying samples with chloride ion, based on relative fluorescence. The controls were: HEPES Buffer (pH 7.4 and osmolarity at standard mOsm=300 (+/−15)); 0.1 mM NaCl (1×HBSS buffer pH7.4); and, a supplemental control against the HBSS buffer in the latter control: HBSS buffer pH 3.0. The fluorescence detection parameters were: 517 nm Excitation/535 nm Emission (+/−2).

It can be seen, therefore, that the TempoChloro™ biosensor system is effective in detecting chloride ions in divergent cell types, including neurons and glial cells, and would be effective in other mammalian or human cell types, including, immortalized, native or induced: pluripotent stem cells, neurons, glial cells, and neural progenitor cells.

The specific methods, procedures and apparatus described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A chloride ion sensor peptide construct comprising: a chloride ion sensing domain having a sequence at least 95% identical to SEQ ID NO: 1; and, a fluorescent reporter domain, wherein the fluorescent reporter domain is adapted to change fluorescent emissions characteristics in response to chloride ion concentration; and wherein the fluorescent reporter domain has a fluorescent emission range of 500 nm to 700 nm and a fluorescent excitation range of 400 nm to 700 nm.

2. The chloride ion sensor peptide construct of claim 1 wherein the fluorescent reporter comprises a sequence at least 95% identical to SEQ ID NO: 3.

3. The chloride ion sensor peptide construct of claim 1 wherein the chloride ion sensing domain binds to chloride ion.

4. The chloride ion sensor peptide construct of claim 1 further including one or more targeting peptide segments with affinity for a cellular target.

5. The chloride ion sensor peptide construct of claim 4 wherein the targeting peptide segments are one or more of: an NLS tag, an ER tag, an endosome tag, a human endosome sequence tag, a ciliary tag, a human synapsin tag, and a human synaptic vesicle tag.

6. A chloride ion sensor peptide construct comprising: a chloride ion sensing domain having a sequence at least 95% identical to SEQ ID NO: 1; and, a fluorescent reporter domain; wherein the fluorescent reporter domain is adapted to change fluorescent emissions characteristics in response to chloride ion concentration; and wherein the fluorescent reporter domain has a fluorescent emission range of 500 nm to 700 nm and a fluorescent excitation range of 400 nm to 700 nm.

7. The chloride ion sensor peptide construct of claim 6 wherein the fluorescent reporter comprises a sequence at least 95% identical to SEQ ID NO: 3.

8. The chloride ion sensor peptide construct of claim 6 wherein the chloride ion sensing domain binds to chloride ion.

9. The chloride ion sensor peptide construct of claim 6 further including one or more targeting peptide segments with affinity for a cellular target.

10. The chloride ion sensor peptide construct of claim 6 wherein the targeting peptide segments are one or more of: an NLS tag, an ER tag, an endosome tag, a human endosome sequence tag, a ciliary tag, a human synapsin tag, and a human synaptic vesicle tag.

* * * * *

SEQUENCE LISTING

```
<160> NUMBER OF SEQ ID NOS: 11

<210> SEQ ID NO 1
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Gly Cys Arg Gly Ser Leu Cys Cys Cys Cys Arg Trp Cys Cys
1               5                   10                  15
```

-continued

Cys Cys Gly Glu Arg Glu Thr Arg Thr Pro Glu Glu Leu Thr Ile Leu
            20                  25                  30

Gly Glu Thr Gln Glu Glu Asp Glu Ile Leu Pro Arg Lys Asp Tyr
        35                  40                  45

Glu Ser Leu Asp Tyr Asp Arg Cys Ile Asn Asp Pro Tyr Leu Glu Val
        50                  55                  60

Leu Glu Thr Met Asp Asn Lys Lys Gly Arg Arg Tyr Glu Ala Val Lys
65                  70                  75                  80

Trp Met Val Val Phe Ala Ile Gly Val Cys Thr Gly Leu Pro Val Ala
                85                  90                  95

Ala Gly Ser Gly Ile Pro Glu Ile Lys Cys Tyr Leu Asn Gly Val Lys
            100                 105                 110

Val Pro Gly Ile Val Arg Leu Arg Thr Leu Leu Cys Lys Val Phe Gly
            115                 120                 125

Val Leu Phe Gly Val Ala Gly Gly Leu Phe Val Gly Lys Glu Gly Pro
        130                 135                 140

Met Ile His Ser Gly Ala Val Val Gly Ala Gly Leu Pro Gln Phe Gln
145                 150                 155                 160

Ser Ile Ser Leu Arg Lys Ile Gln Phe Asn Phe Pro Tyr Phe Arg Ser
                165                 170                 175

Asp Arg Asp Lys Arg Asp Phe Val Ser Ala Gly Ala Ala Ala Gly Val
            180                 185                 190

Ala Ala Ala Phe Gly Ala Pro Ile Gly Gly Thr Leu Phe Ser Leu Glu
            195                 200                 205

Glu Gly Ser Ser Phe Trp Asn Gln Gly Leu Thr Trp Lys Val Leu Phe
        210                 215                 220

Cys Ser Met Ser Ala Thr Phe Thr Leu Asn Phe Phe Arg Ser Gly Ile
225                 230                 235                 240

Gln Phe Gly Ser Trp Gly Ser Phe Gln Leu Pro Gly Leu Leu Asn Phe
                245                 250                 255

Gly Glu Phe Lys Cys Ser Asp Ser Asp Lys Lys Cys His Leu Trp Thr
            260                 265                 270

Ala Met Asp Leu Gly Phe Phe Val Met Met Gly Val Ile Gly Gly Leu
        275                 280                 285

Leu Gly Ala Thr Phe Asn Cys Leu Asn Lys Arg Leu Ala Lys Tyr Arg
        290                 295                 300

Met Arg Asn Val His Pro Lys Pro Lys Leu Val Arg Val Leu Glu Ser
305                 310                 315                 320

Leu Leu Val Ser Leu Val Thr Thr Val Val Phe Val Ala Ser Met
                325                 330                 335

Val Leu Gly Glu Cys Arg Gln Met Ser Ser Ser Ser Gln Ile Ser Asn
            340                 345                 350

Gly Ser Phe Gln Leu Gln Val Thr Ser Glu Asp Val Asn Ser Ser Ile
        355                 360                 365

Lys Thr Phe Phe Cys Pro Asn Asp Thr Tyr Asn Asp Met Ala Thr Leu
        370                 375                 380

Phe Phe Asn Ser Gln Glu Ser Ala Ile Leu Gln Leu Phe His Gln Asp
385                 390                 395                 400

Ala Thr Phe Leu Val Cys Ser Phe Ser Tyr Ile Gly Leu Gly His
            405                 410                 415

Ile Tyr Ser Gly Thr Phe Ala Leu Ile Gly Ala Ala Phe Leu Gly
            420                 425                 430

Gly Val Val Arg Met Thr Ile Ser Leu Thr Ile Ile Leu Ile Glu Ser

```
                435                 440                 445
Thr Asn Glu Ile Thr Tyr Gly Leu Pro Ile Met Val Thr Leu Met Val
            450                 455                 460

Ala Lys Trp Thr Gly Asp Phe Phe Asn Lys Gly Ile Tyr Asp Ile His
465                 470                 475                 480

Val Gly Leu

<210> SEQ ID NO 2
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggcgggct gccgcggcag cctgtgctgc tgctgccgct ggtgctgctg ctgcggcgaa      60
cgcgaaaccc gcaccccgga gaactgacc attctgggcg aaacccagga agaagaagat     120
gaaattctgc cgcgcaaaga ttatgaaagc ctggattatg atcgctgcat taacgatccg     180
tatctggaag tgctggaaac catggataac aaaaaaggcc gccgctatga agcggtgaaa     240
tggatggtgg tgtttgcgat tggcgtgtgc accggcctgc cggtggcggc gggcagcggc     300
attccggaaa ttaaatgcta tctgaacggc gtgaaagtgc cgggcattgt cgcgcctgcgc    360 accctgctgt gcaaagtgtt tggcgtgctg tttggcgtgg cgggcggcct gtttgtgggc     420
aaagaaggcc cgatgattca tagcggcgcg gtggtgggcg cgggcctgcc gcagtttcag     480
agcattagcc tgcgcaaaat tcagtttaac tttccgtatt tcgcagcga tcgcgataaa      540 cgcgattttg tgagcgcggg cgcggcggcg gcgtggcgg cggcgtttgg cgcgccgatt      600
ggcggcaccc tgtttagcct ggaagaaggc agcagctttt ggaaccaggg cctgacctgg      660
aaagtgctgt tttgcagcat gagcgcgacc tttacccctg actttttttcg cagcggcatt      720 cagtttggca gctgggcag cttttcagctg ccgggcctgc tgaactttgg cgaatttaaa      780
tgcagcgata gcgataaaaa atgccatctg tggaccgcga tggatctggg cttttttgtg     840
atgatgggcg tgattggcgg cctgctgggc gcgacccttta actgcctgaa caaacgcctg    900
gcgaaatatc gcatgcgcaa cgtgcatccg aaaccgaaac tggtgcgcgt gctggaaagc     960
ctgctggtga gcctggtgac caccgtggtg gtgtttgtgg cgagcatggt gctgggcgaa    1020
tgccgccaga tgagcagcag cagccagatt agcaacggca gctttcagct gcaggtgacc    1080
agcgaagatg tgaacagcag cattaaaacc ttttttttgcc cgaacgatac ctataacgat    1140
atggcgaccc tgttttttaa cagccaggaa agcgcgattc tgcagctgtt tcatcaggat    1200 gcgaccttc tggtgtgcag ctttaccagc tatattggcc tgggccatat ttatagcggc     1260
acctttgcgc tgattggcgc ggcggcgttt ctgggcggcg tggtgcgcat gaccattagc     1320
ctgaccatta ttctgattga aagcaccaac gaaattacct atggcctgcc gattatggtg     1380
accctgatgg tggcgaaatg gaccggcgat ttttttaaca aaggcattta tgatattcat     1440
gtgggcctg                                                            1449

<210> SEQ ID NO 3
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 3

Met Tyr Thr Asp Cys Lys Glu Phe Ser Asn Thr Tyr His Asn Leu Gly
1               5                   10                  15

Arg Leu Pro Asp Glu Asp Arg His Trp Ser Ala Ser Cys His His His
            20                  25                  30

His His His Met Gly Met Ser Gly Ser Ser Met Ser Val Ile Lys Ser
        35                  40                  45

His Asn Val Met Val Ser Lys Gly Glu Glu Leu Phe Thr Gly Val Val
    50                  55                  60

Pro Ile Leu Val Glu Leu Asp Gly Asp Val Asn Gly His Lys Phe Ser
65              70                  75                  80

Val Arg Gly Glu Gly Glu Gly Asp Ala Thr Asn Gly Lys Leu Thr Leu
                85                  90                  95

Lys Phe Ile Cys Thr Thr Gly Lys Leu Pro Val Pro Trp Pro Thr Leu
            100                 105                 110

Val Thr Thr Phe Gly Tyr Gly Val Ala Cys Phe Ser Arg Tyr Pro Asp
        115                 120                 125

His Met Lys Gln His Asp Phe Phe Lys Ser Ala Met Pro Glu Gly Tyr
    130                 135                 140

Val Gln Glu Arg Thr Ile Ser Phe Lys Asp Asp Gly Thr Tyr Lys Thr
145                 150                 155                 160

Arg Ala Glu Val Lys Phe Glu Gly Asp Thr Leu Val Asn Arg Ile Glu
                165                 170                 175

Leu Lys Gly Ile Asp Phe Lys Glu Asp Gly Asn Ile Leu Gly His Lys
            180                 185                 190

Leu Glu Tyr Asn Phe Asn Ser His Tyr Val Tyr Ile Thr Ala Asp Lys
        195                 200                 205

Gln Lys Asn Ser Ile Lys Ala Asn Phe Lys Ile Arg His Asn Val Glu
    210                 215                 220

Asp Gly Ser Val Gln Leu Ala Asp His Tyr Gln Gln Asn Thr Pro Ile
225                 230                 235                 240

Gly Asp Gly Pro Val Leu Leu Pro Asp Asn His Tyr Leu Ser His Gln
                245                 250                 255

Ser Lys Leu Ser Lys Asp Pro Asn Glu Lys Arg Asp His Met Val Leu
            260                 265                 270

Leu Glu Phe Val Thr Ala Ala Gly Ile Thr Leu Gly Met Asp Glu Leu
        275                 280                 285

Tyr Lys Ser Gly Leu Arg Ser Arg Ala Gln Ala Ser Asn Ser Ala Val
    290                 295                 300

Asp Gly Thr Ala Gly Pro Gly Ser Thr Gly Ser Arg
305                 310                 315

<210> SEQ ID NO 4
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgtatacag actgtaagga attctctaat acatatcaca atctggggag acttcctgat      60
gaggacaggc actggagcgc ctcctgccat catcatcatc accatatggg gatgtctggc     120
tcatctatga gcgtaatcaa gtcccacaat gtcatggtgt caaaagggga agagttgttt     180

```
accggggttg ttcctattct cgtagagttg gacggtgacg tgaatggtca caagttctcc    240
gttcgcggcg aaggagaggg tgatgcaacc aatgggaaac tgaccctgaa attcatatgc    300
acgactggta aacttcctgt accgtggccg acactcgtta ccacgttcgg gtacggagtg    360
gcttgcttct ccagataccc cgaccacatg aaacaacacg acttttttcaa atctgcaatg   420 cccgagggct atgttcagga acggaccata tcttttaagg atgatggaac atataaaaca    480
agggcagaag taaaatttga aggggatact ttggtgaaca ggatagagct caaagggata    540
gattttaagg aggacggaaa tatactgggc cataagcttg agtataattt caactcacac    600
tacgtctata ttacagctga caaacaaaag aacagtatca aagcgaactt caagattcgc    660
cataatgtcg aagatggaag cgtgcaactc gccgaccatt atcagcagaa cactccgata    720
ggcgatggac cagtacttct gcccgacaac cactatttga gtcaccagag taagttgagt    780
aaggacccta acgagaagag agatcacatg gtcttgctcg aatttgtgac tgcagcgggt    840
attaccttgg gaatggacga gctttacaag tctggtctta gatcacgagc acaggcttca    900
aattctgcag tagatggtac agccggaccc gggagcacag gttctaggta a             951
```

```
<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Pro Lys Lys Lys Arg Lys Val
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Asp Glu Leu
1

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (13)..(14)
<223> OTHER INFORMATION: Any residue with a hydrophobic side group

<400> SEQUENCE: 7

Asn Pro Thr Tyr Asp Xaa Xaa Leu Leu Tyr Xaa Xaa Xaa Xaa
```

```
<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (17)..(17)
<223> OTHER INFORMATION: Any amino acid

<400> SEQUENCE: 8

Val Xaa Pro Xaa Arg Val Xaa Pro Lys Val His Pro Ser Ser Thr Ala
1               5                   10                  15

Xaa Glu Gly Gly
            20

<210> SEQ ID NO 9
<211> LENGTH: 31
<212> TYPE: PRT
<213> ORGANISM: Homo sapiens

<400> SEQUENCE: 9

Met Thr Ser Arg Lys Lys Val Leu Leu Lys Val Ile Ile Leu Gly Asp
1               5                   10                  15

Ser Gly Val Gly Lys Thr Ser Leu Met His Arg Tyr Val Asn Asp
            20                  25                  30

<210> SEQ ID NO 10
<211> LENGTH: 571
<212> TYPE: DNA
<213> ORGANISM: Homo sapiens

<400> SEQUENCE: 10
cctgcagggc ccactagtat ctgcagaggg ccctgcgtat gagtgcaagt gggttttagg     60
accaggatga ggcggggtgg gggtgcctac ctgacgaccg accccgaccc actggacaag    120
cacccaaccc ccattcccca aattgcgcat ccctatcag agaggggag gggaaacagg      180 atgcggcgag gcgcgtgcgc actgccagct tcagcaccgc ggacagtgcc ttcgccccg     240 cctggcggcg cgcgccaccg ccgcctcagc actgaaggcg cgctgacgtc actcgccggt    300
cccccgcaaa ctccccttcc cggccacctt ggtcgcgtcc gcgccgccgc cggcccagcc    360
ggaccgcacc acgcgaggcg cgagataggg gggcacgggc gcgaccatct gcgctgcggc    420
gccggcgact cagcgctgcc tcagtctgcg gtgggcagcg gaggagtcgt gtcgtgcctg    480
agagcgcagc tgtgctcctg ggcaccgcgc agtccgcccc gcggctcct ggccagacca     540 cccctaggac cccctgcccc aagtcgcagc c                                   571

<210> SEQ ID NO 11
```

```
<211> LENGTH: 190
<212> TYPE: PRT
<213> ORGANISM: Homo sapiens

<400> SEQUENCE: 11

Met Asp Cys Leu Cys Ile Val Thr Thr Lys Lys Tyr Arg Tyr Gln Asp
1               5                   10                  15

Glu Asp Thr Pro Pro Leu Glu His Ser Pro Ala His Leu Pro Asn Gln
            20                  25                  30

Ala Asn Ser Pro Pro Val Ile Val Asn Thr Asp Thr Leu Glu Ala Pro
        35                  40                  45

Gly Tyr Glu Leu Gln Val Asn Gly Thr Glu Gly Glu Met Glu Tyr Glu
    50                  55                  60

Glu Ile Thr Leu Glu Arg Gly Asn Ser Gly Leu Gly Phe Ser Ile Ala
65                  70                  75                  80

Gly Gly Thr Asp Asn Pro His Ile Gly Asp Asp Pro Ser Ile Phe Ile
                85                  90                  95

Thr Lys Ile Ile Pro Gly Gly Ala Ala Ala Gln Asp Gly Arg Leu Arg
                100                 105                 110

Val Asn Asp Ser Ile Leu Phe Val Asn Glu Val Asp Val Arg Glu Val
            115                 120                 125

Thr His Ser Ala Ala Val Glu Ala Leu Lys Glu Ala Gly Ser Ile Val
        130                 135                 140

Arg Leu Tyr Val Met Arg Arg Lys Pro Pro Ala Glu Lys Val Met Glu
145                 150                 155                 160

Ile Lys Leu Ile Lys Gly Pro Lys Gly Leu Gly Phe Ser Ile Ala Gly
                165                 170                 175

Gly Val Gly Asn Ser Thr Ser Leu Glu Ile Thr Ala Ser Met
            180                 185                 190
```